US 6,538,153 B1

(12) United States Patent
Hirsch et al.

(10) Patent No.: US 6,538,153 B1
(45) Date of Patent: Mar. 25, 2003

(54) METHOD OF SYNTHESIS OF WATER SOLUBLE FULLERENE POLYACIDS USING A MACROCYCLIC MALONATE REACTANT

(75) Inventors: Andreas Hirsch, Rathsberg (DE); Uwe Reuther, Nürnberg (DE)

(73) Assignee: C Sixty Inc., Toronto (CA)

( * ) Notice: Subject to any disclaimer, the term of this patent is extended or adjusted under 35 U.S.C. 154(b) by 0 days.

(21) Appl. No.: 09/962,492

(22) Filed: Sep. 25, 2001

(51) Int. Cl.[7] .................. C07C 69/76; C07C 63/00; C07D 305/00

(52) U.S. Cl. ............... 560/82; 562/405; 549/263

(58) Field of Search ............. 560/82; 562/405; 549/263

(56) References Cited

U.S. PATENT DOCUMENTS

| 5,739,376 | A |   | 4/1998  | Bingel  ............ 560/51 |
| 6,162,926 | A |   | 12/2000 | Murphy et al. ......... 548/417 |
| 6,303,760 | B1 | * | 10/2001 | Dorn et al. ............ 534/11 |
| 6,452,037 | B1 | * | 9/2002  | Chiang ............. 560/102 |

FOREIGN PATENT DOCUMENTS

WO      WO97/46227      12/1997

* cited by examiner

Primary Examiner—Deborah C. Lambkin
(74) Attorney, Agent, or Firm—Williams, Morgan & Amerson, P.C.

(57) ABSTRACT

A method for synthesizing compounds of the formula

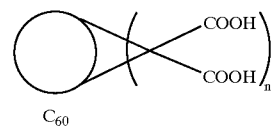

where $C_{60}$ is a $C_{60}$ fullerene. The method comprises the steps of forming a macrocyclic malonate compound of the formula

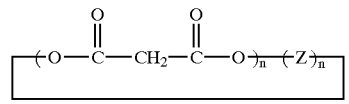

where each Z is the same or different and is a straight-chain or branched-chain aliphatic radical having from 1–30 carbon atoms which may be unsubstituted or monosubstituted or polysubstituted by identical or different substitutents, in which radicals up to every third $CH_2$ unit can be replaced by O or NR where R is alkyl having 1–20 carbon atoms or a chain containing unsubstituted or substituted aryl or other cyclic groups and n is an integer from 2 to 10; reacting said macrocyclic malonate compound with $C_{60}$ to form an adduct of the formula

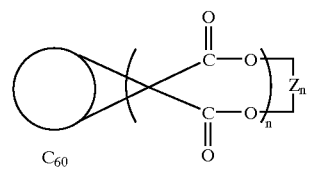

where the Z radicals are linked together to form said macrocycle adduct; and hydrolyzing said macrocycle adduct to form a compound of the formula

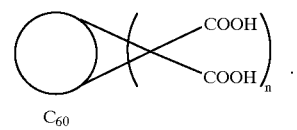

18 Claims, 12 Drawing Sheets

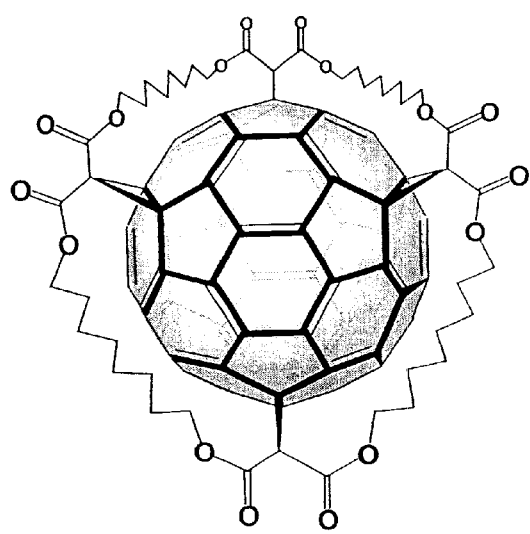 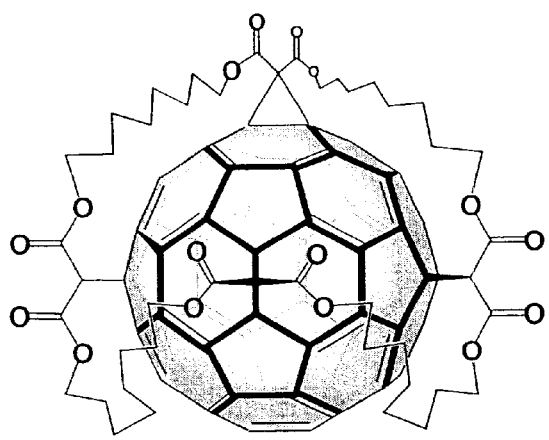
Fig. 12a
Fig. 12b

METHOD OF SYNTHESIS OF WATER SOLUBLE FULLERENE POLYACIDS USING A MACROCYCLIC MALONATE REACTANT

FIELD OF THE INVENTION

The invention relates generally to methods for the synthesis of substituted fullerene compounds and in particular to methods for the synthesis of carboxylated buckminsterfullerene compounds having utility as antioxidants and neuroprotective compounds. Even more specifically, the invention relates to methods for the synthesis of bis, tris and higher adducts of $C_{60}$ having very high regioselectivity and product yield.

BACKGROUND OF THE INVENTION

Multiply-substituted fullerenes are useful for discovery of new pharmaceuticals. Murphy et al., U.S. Pat. No. 6,162, 926, disclose multiply substituted fullerenes and describe their use in combinatorial libraries. The compounds have pharmaceutical, materials science and other utilities. FIGS. 1 and 2 are schematic representations of the bisadducts and trisadducts, respectively, disclosed in Murphy et al.

Using malonate groups ($E^1$—$CH_2$—$E^2$) and the so-called Hirsch-Bingle reaction, fullerene compounds can be synthesized with groups substituted at many different sites. Wilson et al., Organic Chemistry of Fullerenes; Fullerenes: Chemistry, Physics and Technology, Kadish, K. M. and Ruoff, R. S., eds., John Wiley and Sons, New York, 2000, pp. 91–176.

Bingel, U.S. Pat. No. 5,739,376, describes the following reaction:

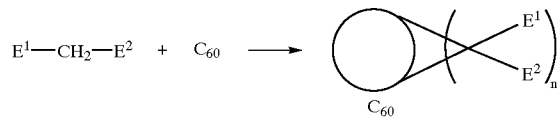

where $E^1$ and $E^2$ are COOH, COOR or other radicals and n is 1–10. Several of these compounds, e.g. the so-called carboxylated buckminsterfullerenes have become potentially useful as pharmaceutical candidates for the protection of neurotoxic injury. Choi and Dugan et al., PCT/EP97/02679. FIG. 3 depicts a trisadduct (C3) obtained by Choi.

The large scale synthesis of C3 is difficult since a multitude of isomers are produced and the preparation requires HPLC separation of the desired isomer for use as a therapeutic. One way to control the substitution on the $C_{60}$ is by the so-called tether-directed addition process. Investigators have tried linking a multitude of chemically reactive groups together so that they react with the $C_{60}$ only at one site. A complete survey of these attempts is found in Wilson, et al.

It is known that water soluble fullerene hexaacids like those shown in FIGS. 4 and 5 are effective antioxidants and have neuroprotective properties. It is desirable to produce larger quantities of these compounds for clinical studies.

The usual synthetic precursors for the compounds of FIGS. 4 and 5 are the hexaesters. These can be made by stepwise reaction of $C_{60}$ with diethylbromomomalonate with intermediate purification by flash chromatography. The reaction has been described in Bingel., Chem. Ber. 1993, 126, 1957. Due to the stepwise synthesis and the tedious chromatographic purifications, the yield of trisadducts is low. This reaction is thus unsuitable for large scale production.

Diederich et al. have developed a method for the one-step production of e,e,e- and trans-3, trans-3, trans-3 trisadducts from $C_{60}$ using a cyclotriveratrylene tether. G. Rapenne et al., Chem. Commun. 1999, 1121. Although this reaction leads to a clean formulation of trisadducts, the overall yield is still quite low, e.g. 11% trans-3, trans-3, trans-3- and 9% e,e,e-isomer, and the tether system itself is only accessible in a multi-step synthesis.

While some success has been achieved using these methods to link one or more reactive groups to a single fullerene, more effective processes are required if multiply substituted fullerenes are to be used in drug discovery.

OBJECTS OF THE INVENTION

It is a primary object of the invention to provide methods for producing water soluble fullerene polyacids.

It is a further object of the invention to provide methods for producing water-soluble fullerene hexaacids for use as neuroprotectant therapeutic compounds.

SUMMARY OF THE INVENTION

The invention is broadly in a method for synthesizing compounds of the formula

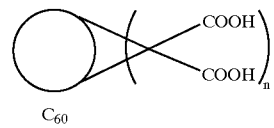

where $C_{60}$ is a $C_{60}$ fullerene.

The method comprises the steps of forming a macrocyclic malonate compound of the formula

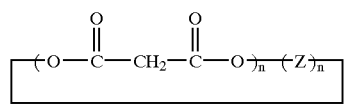

where each Z is the same or different and is a straight-chain or branched-chain aliphatic radical having from 1–30 carbon atoms which may be unsubstituted or monosubstituted or polysubstituted by identical or different substitutents, in which radicals up to every third $CH_2$ unit can be replaced by O or NR where R is alkyl having 1–20 carbon atoms or a chain containing unsubstituted or substituted aryl or other cyclic groups and n is an integer from 2 to 10; reacting said macrocyclic malonate compound with $C_{60}$ to form a macrocycle adduct of the formula

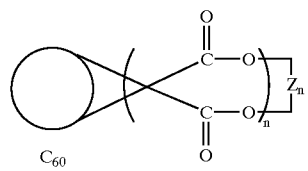

where the Z radicals are linked together to form said macrocycle adduct; and hydrolyzing said macrocycle adduct to form a compound of the formula

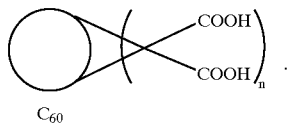

$C_{60}$

BRIEF DESCRIPTION OF THE DRAWINGS

FIG. 12 is a schematic representation of the structure of the macrocycle trans-1,(IV$^1$)cis-3,(IV$^4$)cis-3-(a) and trans-1,e',e"-(b) tetraadducts.

DETAILED DESCRIPTION OF THE INVENTION

The Methods of the Invention

The invention is broadly in a method for synthesizing compounds of the formula

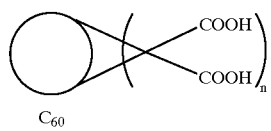

$C_{60}$ where $C_{60}$ is a $C_{60}$ fullerene.

The method comprises the steps of forming a macrocyclic malonate compound of the formula

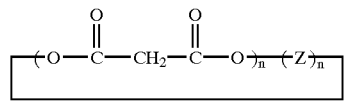

where each Z is the same or different and is a straight-chain or branched-chain aliphatic radical having from 1–30 carbon atoms which may be unsubstituted or monosubstituted or polysubstituted by identical or different substitutents, in which radical up to every third $CH_2$ unit can be replaced by O or NR where R is alkyl having 1–20 carbon atoms or a chain containing unsubstituted or substituted aryl or other cyclic groups and n is an integer from 2 to 10; reacting said macrocyclic malonate compound with $C_{60}$ to form a macrocycle adduct of the formula

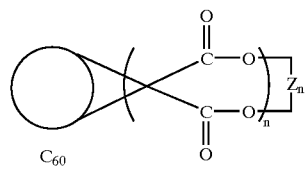

$C_{60}$ where the Z radicals are linked together to form said macrocycle adduct; and hydrolyzing said macrocycle adduct to form a compound of the formula

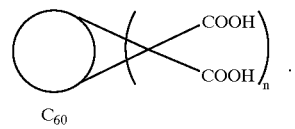

$C_{60}$

It has now been discovered that linking the malonate reactive groups in a ring and using the macrocycle to react with $C_{60}$ leads to improved yields of specific fullerene isomers and avoids the production of multiple undesireable addition isomers. It is possible, for example, to link two, three, four or five malonate groups in a ring, as shown in FIG. 7.

Figure 5:
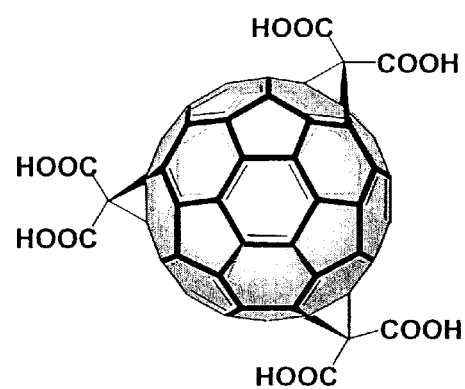
Figure 6:
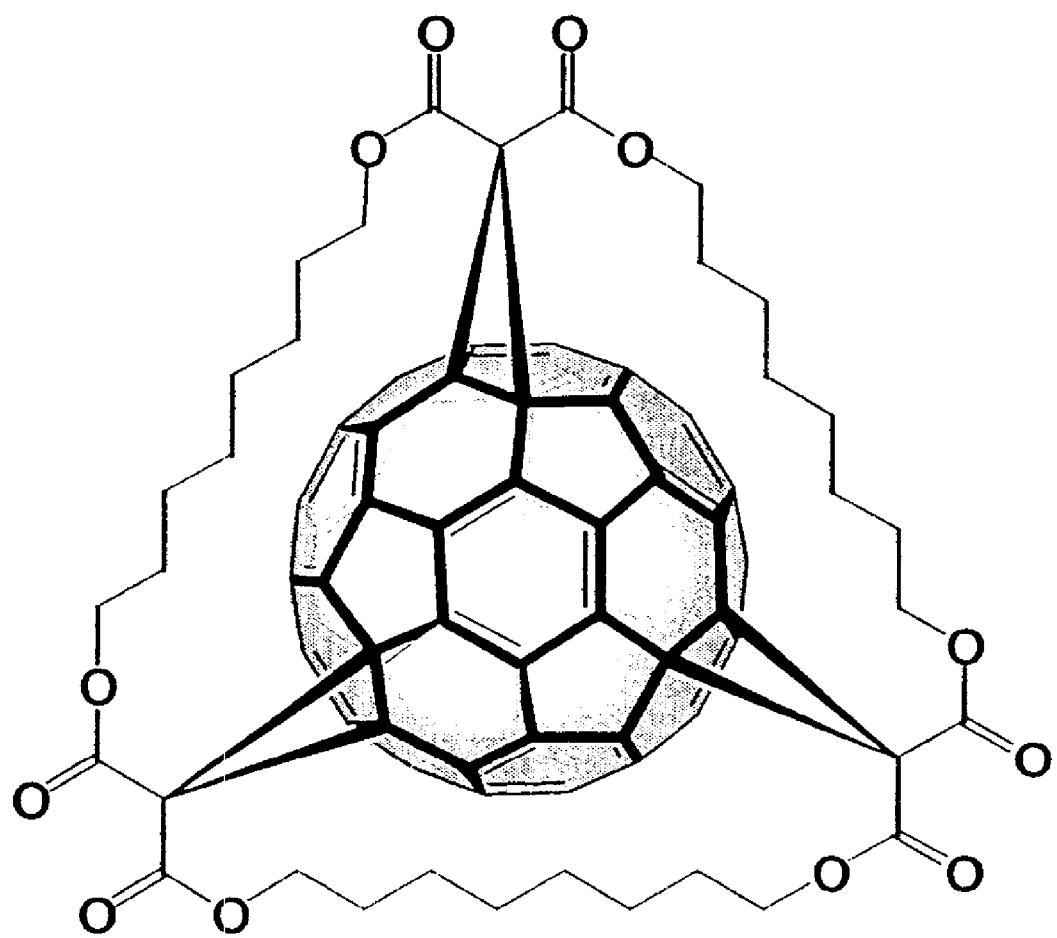
FIG. 6 is a schematic representation of a macrocycle e,e,e-trisadduct prepared according to the invention.

Macrocycles with three malonate units react cleanly with $C_{60}$ to form trisadducts with high regioselectivity and in a typical reaction, an isolable yield of about 60 percent. The regiochemistry of the reaction can be "adjusted" between e,e,e and trans-3, trans-3, trans-3 by altering the chain length of the alkanediol used to link the malonate reactive groups. Product purities of greater than 90 percent can be obtained by flash chromatography, the main impurity being the other regioisomers. The reaction of $C_{60}$ with macrocycle 7B yields the macrocycle e,e,e-trisadduct as shown in FIG. 6. The macrocycle trisadducts thus obtained can be quantitatively hydrolyzed with sodium hydride to yield the water soluble hexaacids of FIGS. 4 and 5.

The macrocycle malonate compound is synthesized by reaction of a malonyl derivative, e.g. dichloride with a bifunctional moiety, e.g. a glycol. Methods to prepare such compounds are disclosed in Singh, J. Chem. Res. 1988, 132–133 and Singh, J. Chem. Res. 1989. In preferred embodiments, malonyl chloride is reacted with an alkanediol having from 8–18 carbon atoms. Octanediol is a preferred species. A mixture of macrocycles of different ring sizes is obtained, and these can be separated by flash chromatography. FIGS. 7A–7D depict the several different macrocycles obtained from the reaction of malonyl dichloride with octanediol. The relative yields among these different macrocycles can be adjusted by altering the concentration of the reaction mixture.

In one embodiment of the invention the tetraacids of the formula

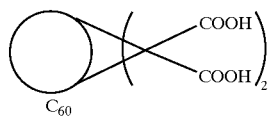

are formed by synthesizing a macrocyclic malonate compound of the formula

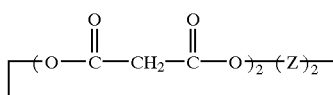

where Z is octanediol; reacting said macrocyclic malonate compound with $C_{60}$ to form the macrocycle adduct of the formula

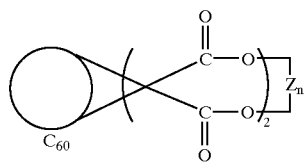

where the Z radicals are linked together to form said macrocycle adduct; and hydrolyzing said macrocycle adduct to form the tetraacids of the formula

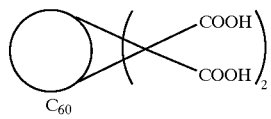

In a preferred embodiment of the invention the hexaacids of the formula

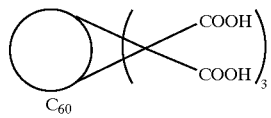

are formed by synthesizing a macrocyclic malonate compound of the formula

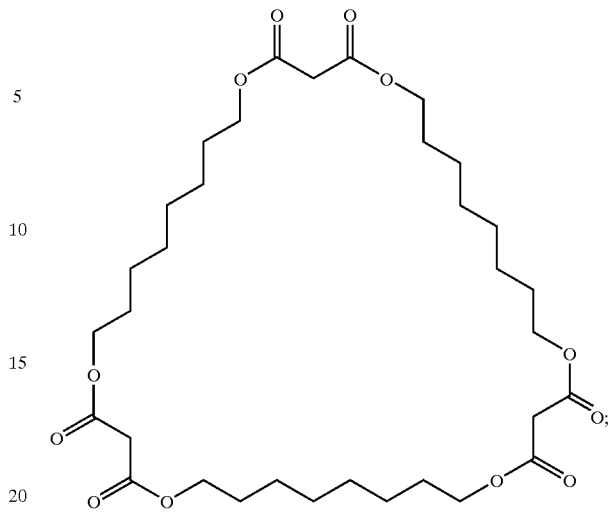

reacting said macrocyclic malonate compound with $C_{60}$ to form the macrocyclic adduct of the formula

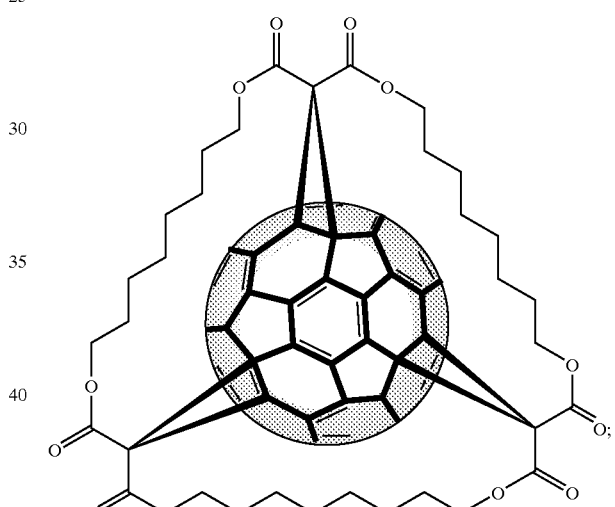

and hydrolyzing said macrocyclic adduct to form the hexaacids of the formula

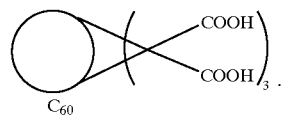

Figure 10A:
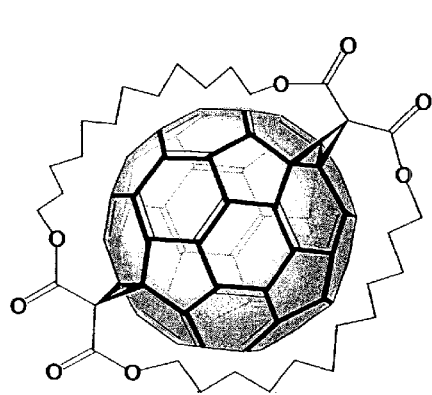
FIG. 10 sets forth schematic representations of the structures of the trans-3- (a) and e- (b) bisadducts and the mixed macrocycle (c).
Figure 10B:
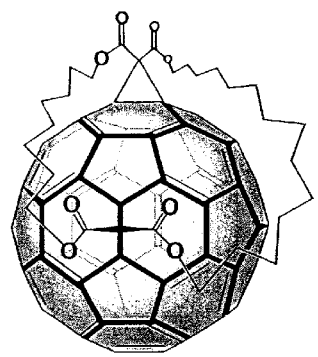
Figure 10C:
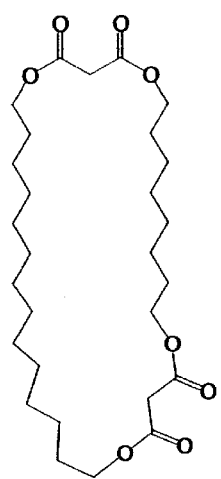

Other fullerene adducts can be synthesized using macrocyclic malonate compounds. FIG. 10 depicts two new macrocyclic bisadducts. Macrocycle bisadduct (a), having a trans-3 addition pattern, has been synthesized by reaction of $C_{60}$ with a $C_{12}$ macrocycle obtained from dodecanediol and malonyl dichloride. Macrocycle bisadduct (b), having an e addition pattern, has been synthesized from macrocycle (c) which contains $C_8$ and $C_{14}$ units. Macrocyle (c) was synthesized using a mixture of octanediol and tetradecanediol. It is also possible to select $C_S$ symmetric addition patterns by this method.

Figure 11:
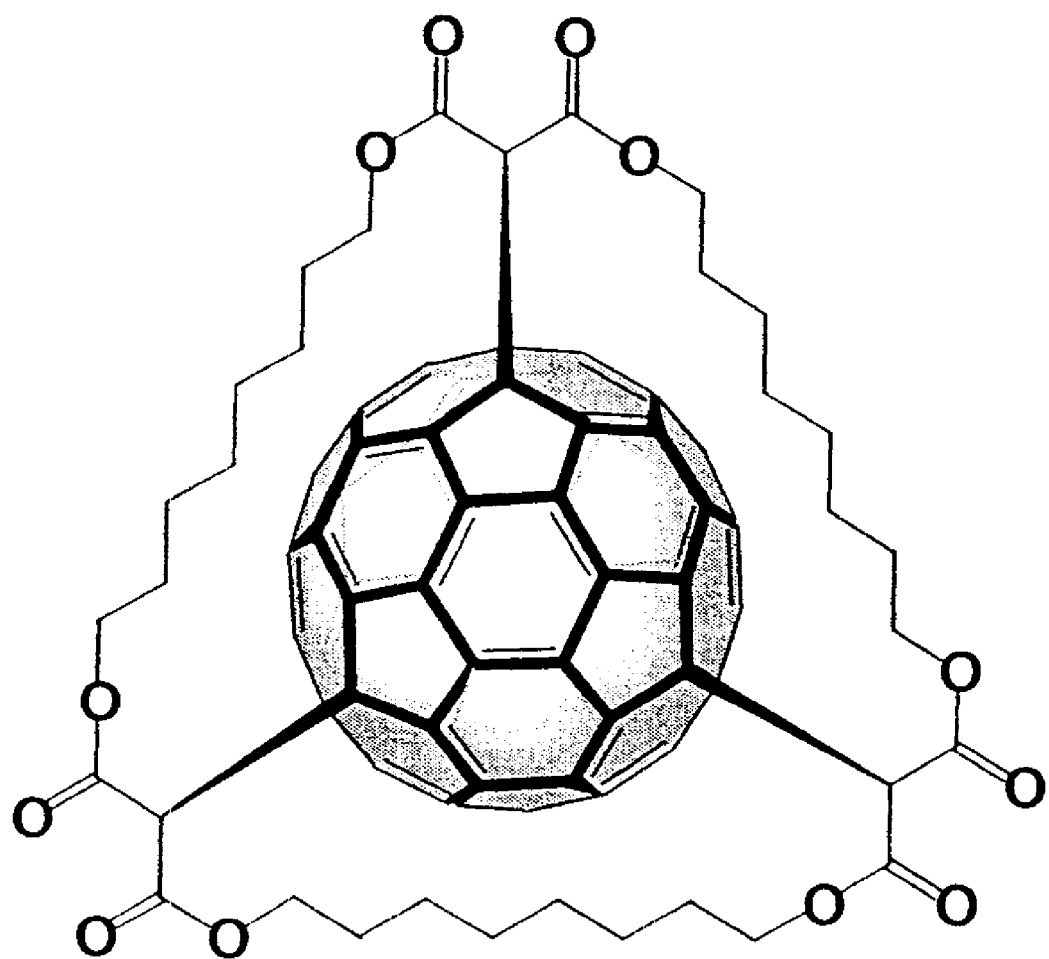
FIG. 11 is a schematic representation of the structure of the macrocycle trans-4, trans-4, trans-4-trisadduct.

A byproduct of the synthesis of the macrocycle e,e,e-trisadduct of FIG. 6 is the hitherto unknown macrocycle trans-4,trans-4,trans-4-trisadduct depicted in FIG. 11. FIG. 12 depicts macrocycle tetraadducts (a) and (b) which were synthesized by the reaction of the macrocycle of FIG. 7C with $C_{60}$. They have trans-1,$(IV^1)$cis-3,$(IV^4)$cis-3- and trans-1,e',e"-addition patterns, respectively.

Figure 13A:
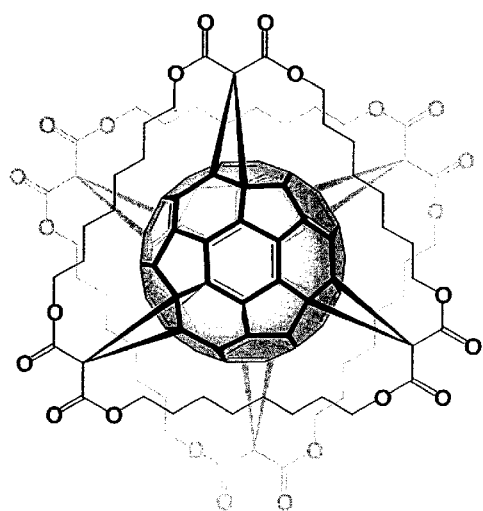
FIG. 13 is a schematic representation of the structures of the macrocycle hexaadducts (a) and (b).
Figure 13B:
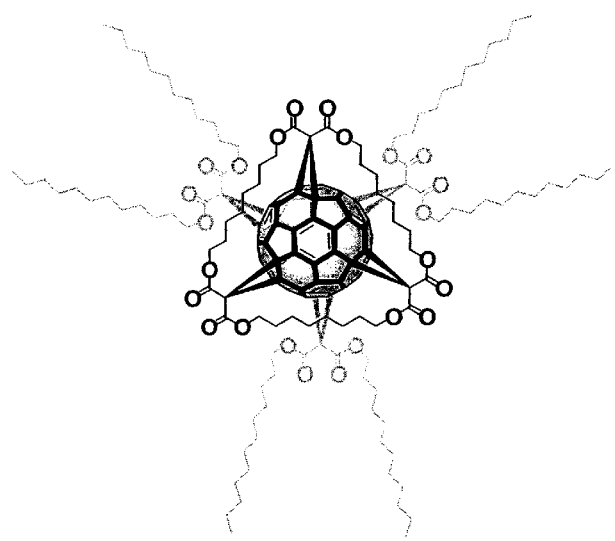

It is also possible to obtain the macrocycle hexaadducts of FIG. 13 with two units of macrocycle 7B, either by stepwise synthesis over the macrocycle trisadduct of FIG. 6 or directly from $C_{60}$ using two equivalents of macrocycle 7B. Mixed macrocycle hexaadducts like 13b are synthesized by the reaction of the macrocycle trisadduct of FIG. 6 with an acrylic malonate under the usual reaction conditions and activation with DMA.

Figure 1:
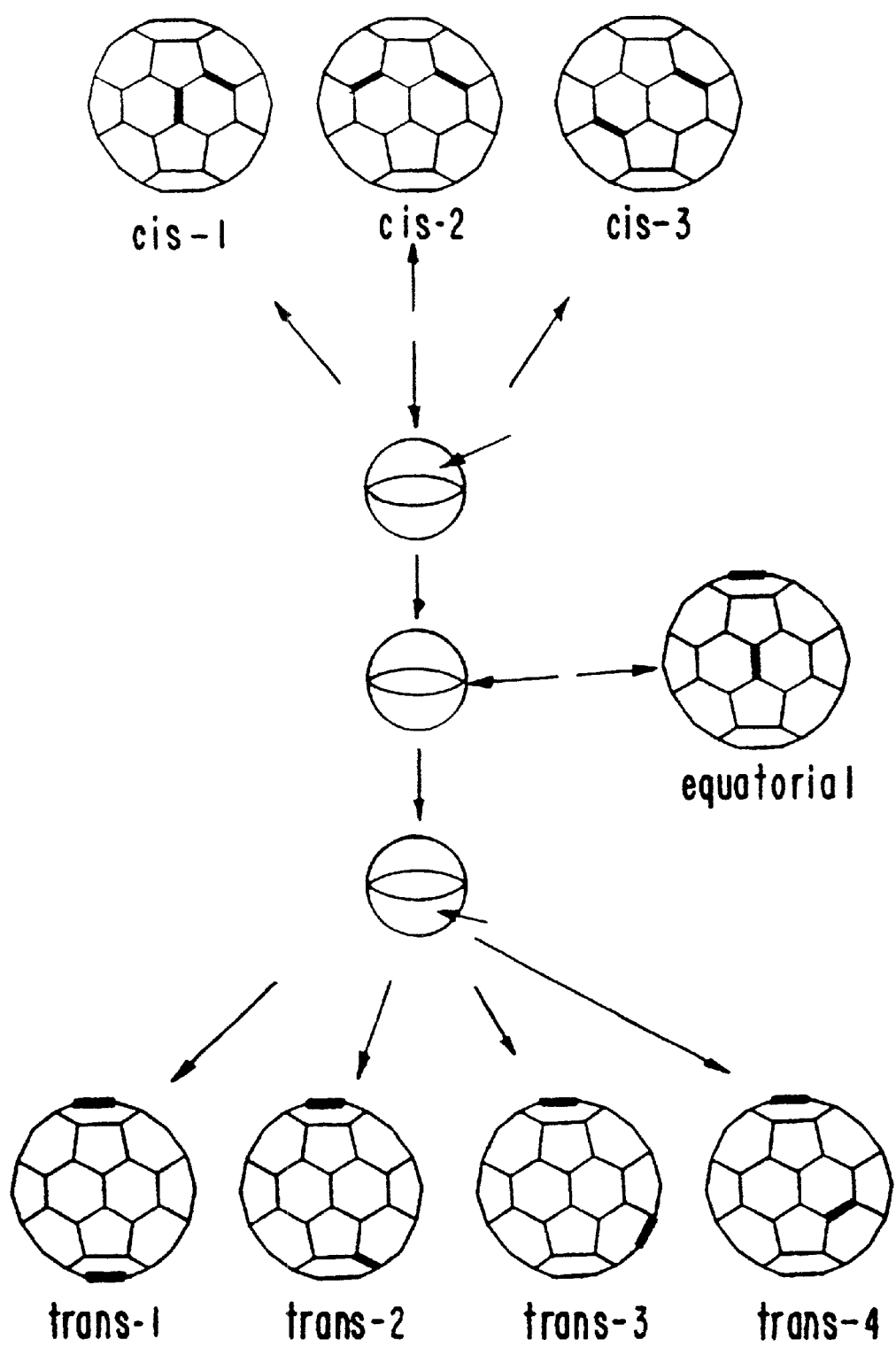
FIG. 1 is a schematic representation of $C_{60}$ bis-adducts prepared by the methods of Murphy et al., U.S. Pat. No. 6,162,926.
Figure 2:
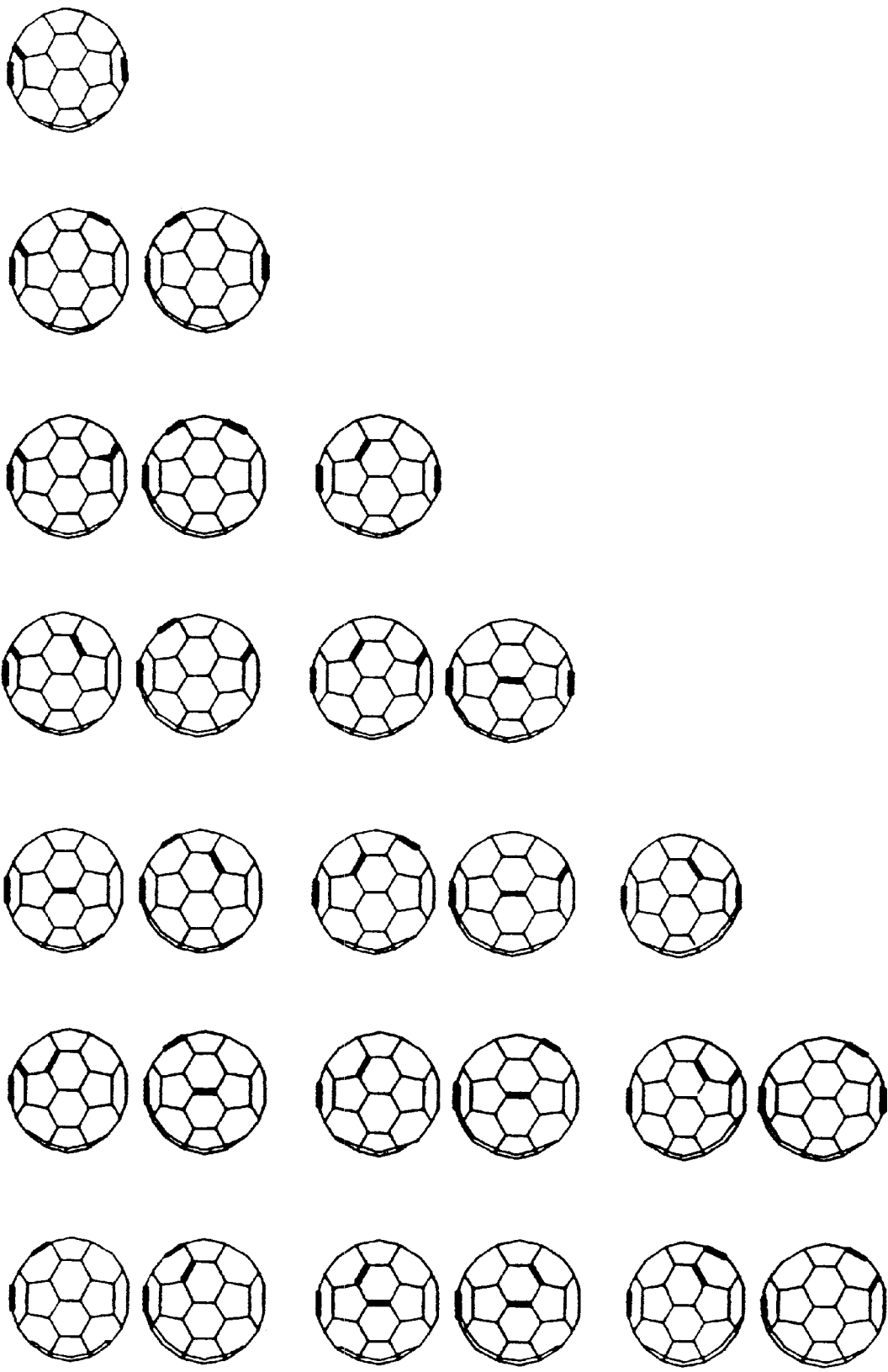
FIG. 2 is a schematic representation of $C_{60}$ tris-adducts prepared by the methods of Murphy et al., U.S. Pat. No. 6,162,926.
Figure 3:
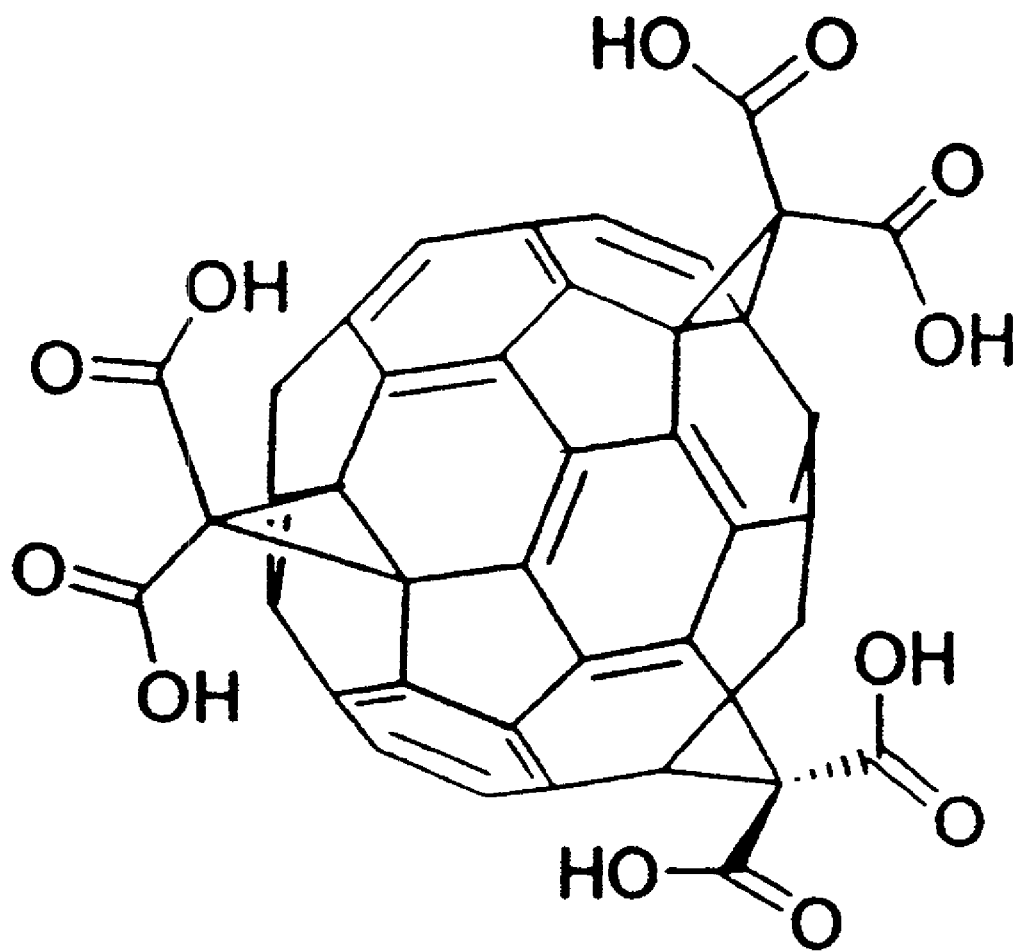
FIG. 3 is a schematic representation of the $C_{60}$ trisadduct prepared by the methods of Choi, International Application No. PCT/EP97/02679.
Figure 4:
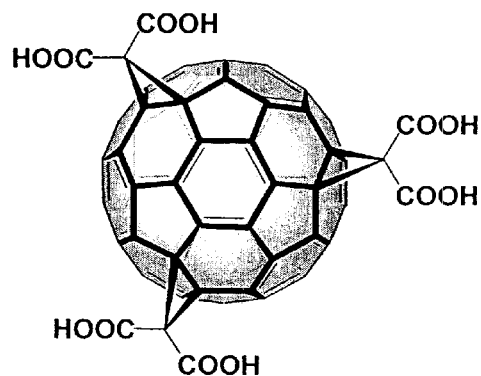
FIGS. 4 and 5 are schematic representations of the e,e,e - (1) and trans-3, trans-3, trans-3-(2) hexaacids of $C_{60}$.

In the following Examples, the hexaacid of FIG. 4 is obtained by the reaction of $C_{60}$ with macrocycle 7B and subsequent hydrolysis. Other reactions follow the same principle.

EXAMPLES

Figure 7A:
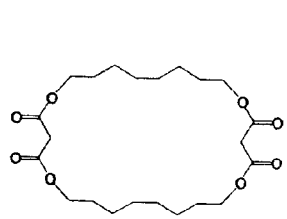
FIG. 7 is a schematic representation of the macrocycles obtained from malonyl dichloride and octanediol by the methods of the invention.
Figure 7B:
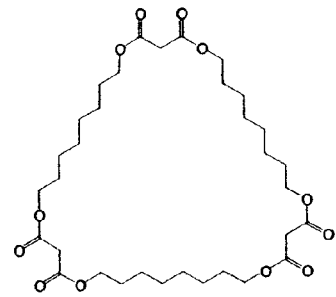
Figure 7C:
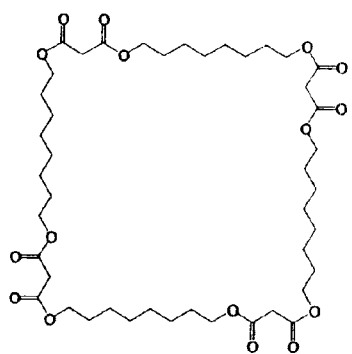
Figure 7D:
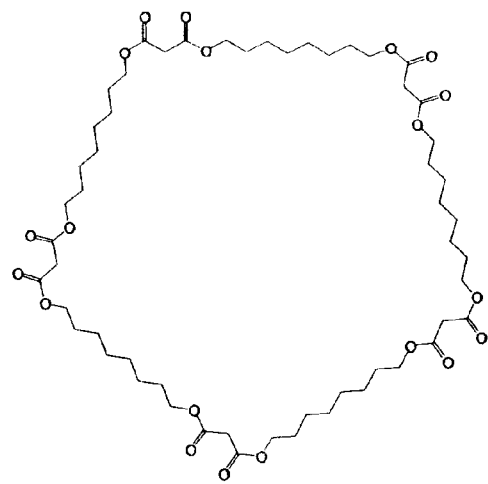
Figure 8A:
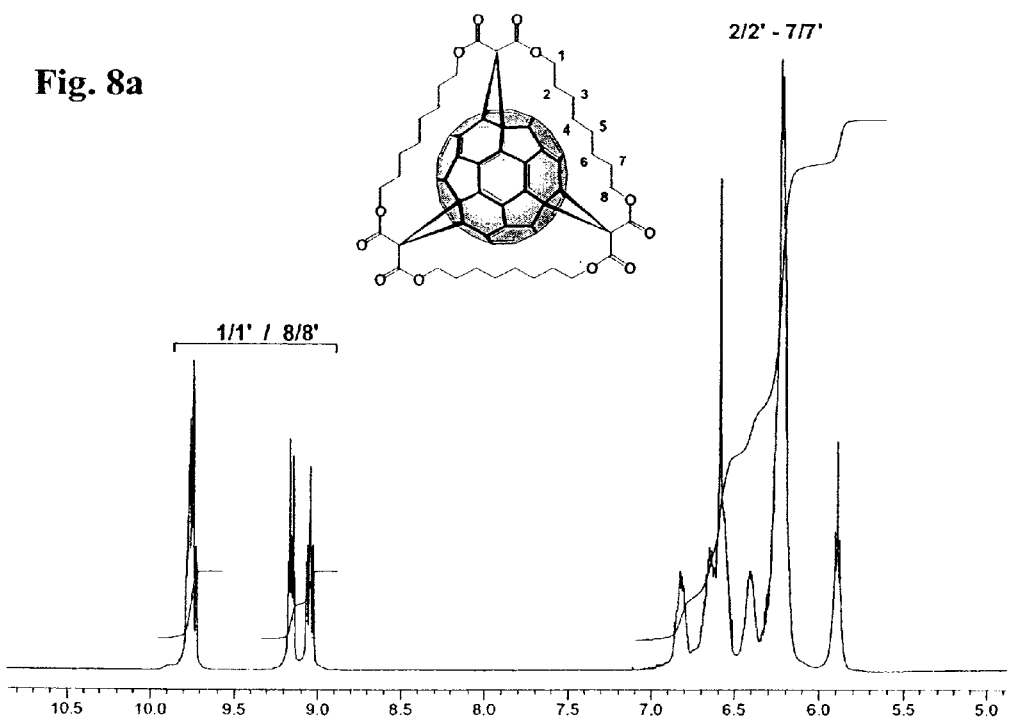
FIG. 8a depicts the $^1H$ NMR spectra of the macrocycle e,e,e-trisadduct of FIG. 6.
Figure 8B:
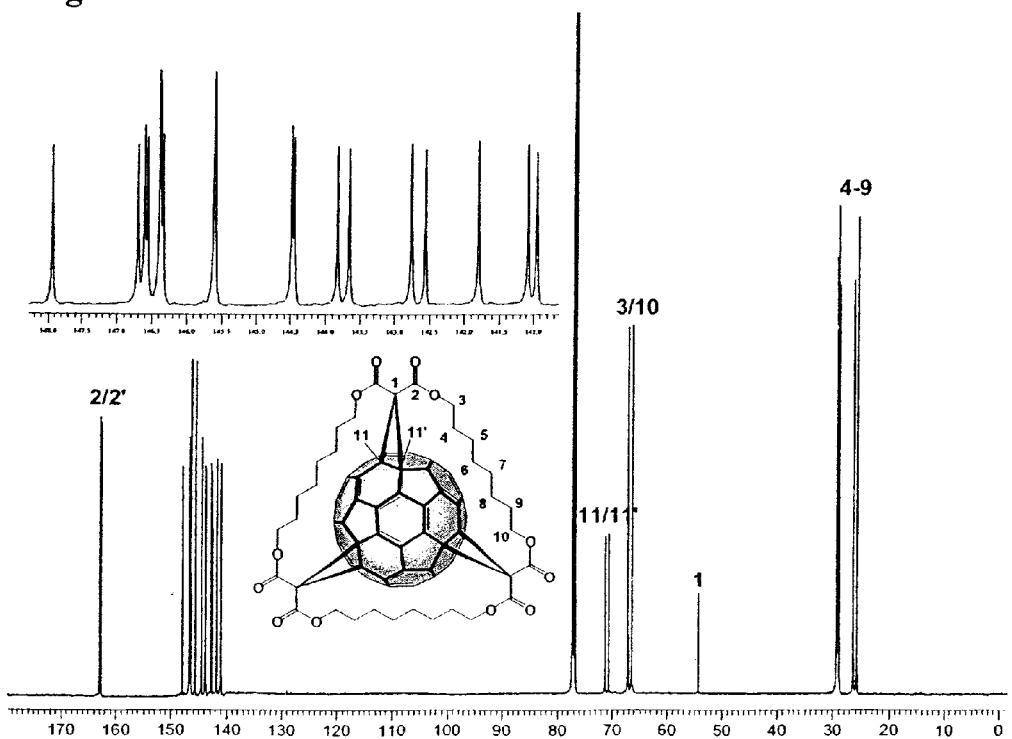
FIG. 8b depicts the $^{13}C$ NMR spectra of the macrocycle e,e,e-trisadduct of FIG. 6.
Figure 9A:
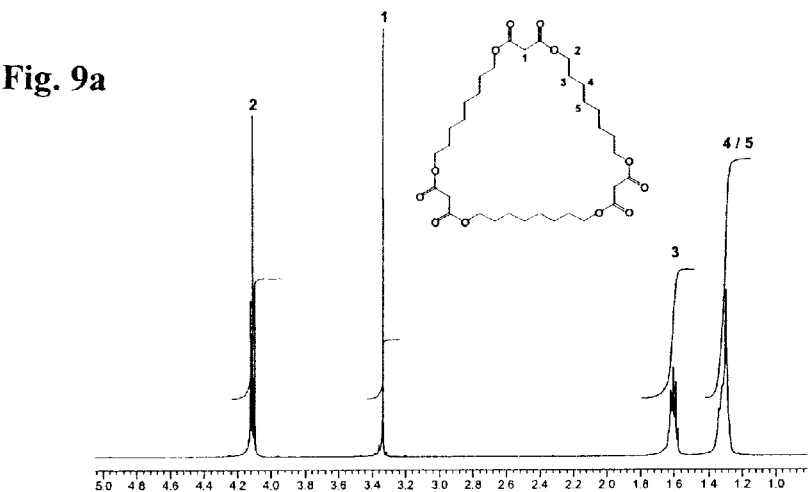
FIG. 9a depicts the $^1H$ NMR spectra of the macrocycle of FIG. 7.
Figure 9B:
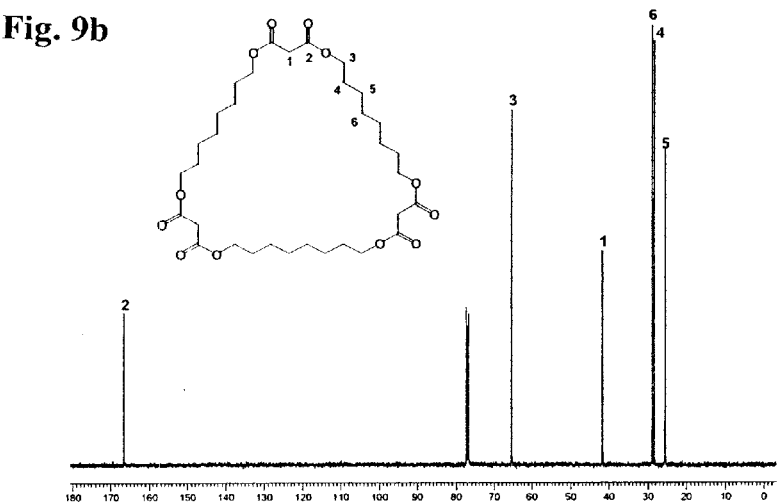
FIG. 9b depicts the $^{13}C$ NMR spectra of the macrocycle of FIG. 7.
Figure 9C:
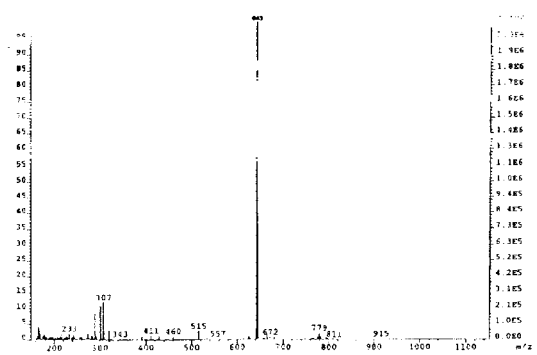
FIG. 9c depicts the mass spectrum of the macrocycle of FIG. 7.

Synthesis of the Macrocycle of FIG. 7B

The following reaction was carried out:

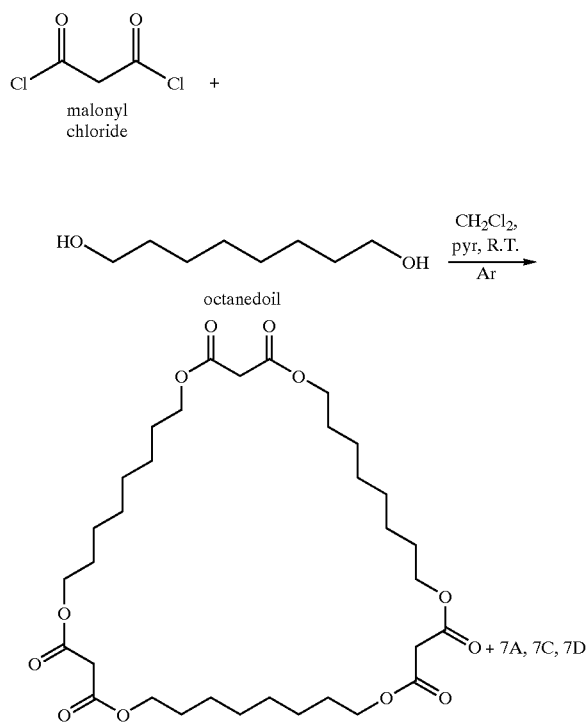

In a dry 2L round bottomed flask equipped with gas inlet, 500 ml dropping funnel and magnetic stirrer, 2.00 g (13.7 mmol/1.00 eq.) octanediol were dissolved under argon in 1L of dry dichloromethane. To this solution 2.16 g (27.3 mmol/2.22 ml/2.00 eq.) pyridine were added. Subsequently, a solution of 3.85 g (27.3 mmol/2 ml/2.00 eq.) malonyl dichloride in 500 ml of dry dichloromethane was added dropwise over a period of 8 hours. After stirring for two days at room temperature the mixture was concentrated with a rotary evaporator and filtered over a silica plug (6×6 cm) with $CH_2CL_2$/ETOAc 90:10 to remove polymeric material and pyridine salts. The solution was evaporated and the resulting slightly yellow crude product was separated by flash chromatography on silica gel (6×35 cm/$CH_2CL_2$/EtOAc 90:10). The order of elution of the compounds is 7A, 7B, 7C and 7D. The product fractions were evaporated to dryness and left colorless solids (7A and 7B) and oils (7B and 7D).

The yields obtained were as follows:

| | | | |
|---|---|---|---|
| 462 mg | 7A | (1.08 mmol), | 15.8% |
| 251 mg | 7B | (0.390 mmol), | 8.6% |
| 114 mg | 7C | (0.133 mmol), | 3.9% |
| 59.1 mg | 7D | (0.0552 mmol), | 2.0% |
| | Total yield of macrocycles: | | 30.3% |

Spectroscopic Data for the macrocycle of FIG. 7B:

$^1$H NMR (500 MHz, $CDCL_3$) δ[ppm]=4.12 (t, 12 H, $^3J$=6.71), 3.34 (s, 6 H), 1.61 (tt, 12 H, $^3J$=6.71), 1.30 (m, 24 H)

$^{13}$C NMR (125.7 MHz, $CDC_{13}$) δ[ppm]=166.6 (6 C, C=O), 65.5 (6 C, O—$CH_2$), 41.8 (3 C, CO—$\underline{C}$H2—CO), 28.9 (6 C, $CH_2$), 28.4 (6 C, $CH_2$), 25.6 (6 C, $CH_2$)

MS (FAB/NBA) m/z 643 ($M^+$+H)

IR (NaCl, Film) ν[$cm^{-1}$]=2933, 2858, 1735, 1466, 1413, 1388, 1330, 1272, 1152, 1013, 666

Synthesis of the e,e,e-Trisadduct of FIG. 6

The following reaction was carried out:

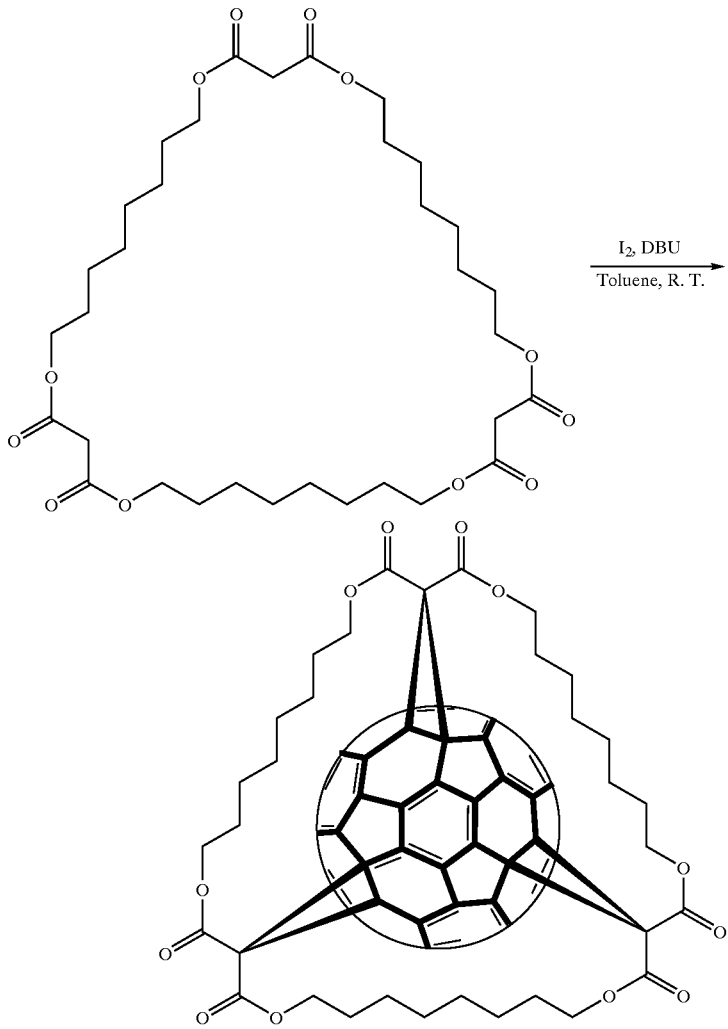

In a dry 1L round bottomed flask equipped with gas inlet, 250 ml dropping funnel and magnetic stirrer 255 mg (0.354 mmol/1.0 eq.) $C_{60}$ were dissolved under argon in 400 ml of dry toluene. Subsequently, 205 mg (0.319 mmol/0.9 eq.) of the macrocycle 7B and 243 mg (0.956 mmol/2.7 eq.) of iodine were added to the solution. Then, a solution of 404 mg (2.65 mmol/7.5 eq./397 μl) DBU in 160 ml of dry toluene was added dropwise over a period of 3 hours. The color of the solution turned a deep orange. After additional stirring at room temperature for about 10 min., the raw mixture was subjected to flash chromatography on silica gel (6×25 cm). Traces of $C_{60}$ and other impurities were eluted with toluene. The eluant was then changed to toluene/ethylacetate 98:2 and the trisadduct of FIG. 6 was eluted as a bright orange band. The product fraction was evaporated to dryness on a rotary evaporator. If necessary, the product can be precipitated from $CH_2Cl_2$/pentane and dried in a high vacuum at 50° C.

The yield obtained was as follows: 254 mg (0.186 mmol), 58.6%

Spectroscopic Data for the e,e,e,-transadduct:

$^1$H NMR (500 MHz, CDC13) δ[ppm]=4.72 (m, 6 H), 4.12 (dt, 3 H), 4.00 (dt, 3 H), 1.80 (m, 3 H), 1.60 (m, 3 H), 1.50 (m, 6 H), 1.35 (m, 3 H), 1.20 (m, 18 H), 0.86 (m, 3 H)

$^{13}$C NMR (125.7 MHz, $CDCL_3$) δ[ppm]=162.88 (3 C, C=O), 162.65 (3 C, C=O), 147.95 (3 C), 146.70 (3 C)146.61 (3 C), 146.57 (3 C), 146.38 (6 C), 146.34 (3 C), 145.61 (6 C), 144.50 (3 C), 144.46 (3 C), 143.83 (3 C), 143.67 (3 C), 142.76 (3 C), 142.57 (3 C), 141.80 (3 C), 141.09 (3 C), 140.96 (3 C), 71.30 (3 C), $C_{60}$-sp3), 70.62 (3 C, $C_{60}$-sp$^3$), 67.17 (3 C, O—C<u>H</u>2), 66.41 (3 C, O—C<u>H</u>2), 54.27(3 C, CO—<u>C</u>—CO), 29.36 (3 C, CH2), 29.19 (3 C, CH2), 29.03 (3 C, $CH_2$), 28.94 (3 C, $CH_2$), 26.35 (3 C, $CH_2$), 25.71 (3 C, CH2)

MS (FAB/NBA) m/z 1357 (M$^+$), 720 ($C_{60}^+$)

IR (KBr) v.[cm$^{-1}$]=2928, 2855, 1747, 1458, 1384, 1273, 1254, 1233, 1214, 1178, 1104, 1065, 741, 714, 704, 664, 528, 522

UV/VIS ($CH_2Cl_2$) λmax (ε)=251 (82200), 281 (59600), 305 (43900), 380 (5900), 481 (4000), 565 (1300)

Synthesis of the e,e,e-Hexaacid of FIG. 4

The following reaction was carried out:

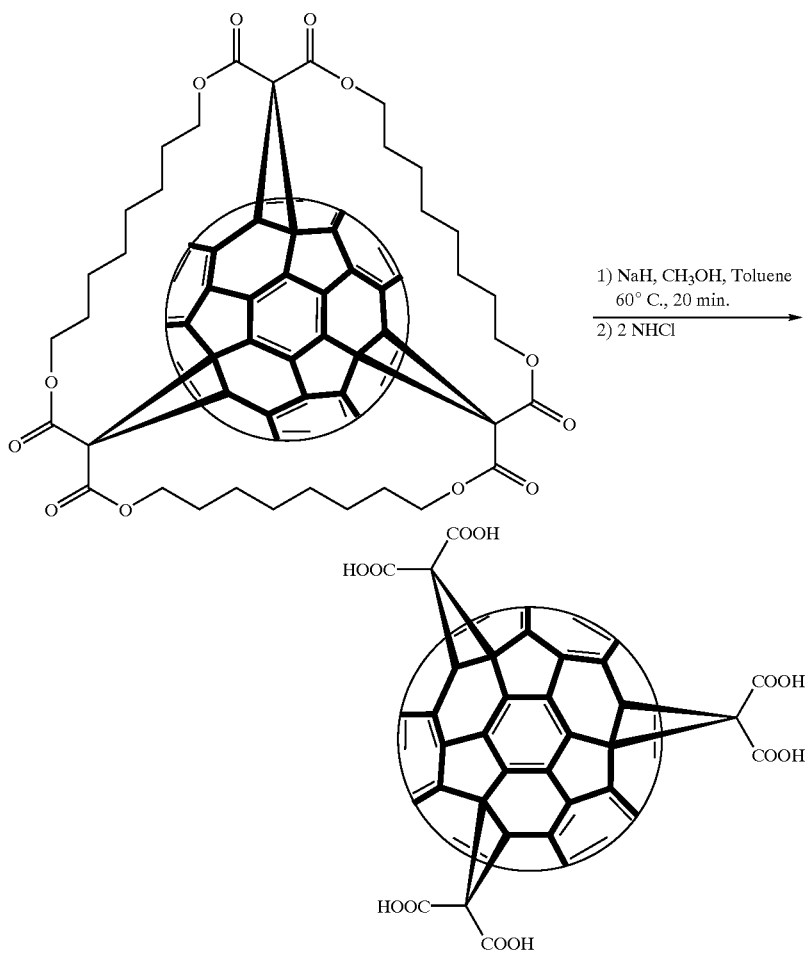

In a 25 ml round bottomed flask equipped with a magnetic stirrer, 23.7 mg (0.0175 mmol/1.0 eq.) of the trisadduct of FIG. 6 were dissolved in 15 ml toluene. 5.3 mg (0.22 mmol/13 eq.) sodium hydride, previously washed with pentane, were added to the solution. The mixture was stirred in an oil bath preheated to 60° and 200 µl of $CH_3OH$ were added in portions of 50 µl. After 20 min. at 60° C. the acid salt had completely precipitated and the mixture was filtered directly through a small porcelain filter crucible. The residue was washed twice with pentane. Subsequently, the precipitate was twice stirred thoroughly with 1.5 ml of 2 N HCL directly in the crubible. The orange residue was dried in a high vacuum.

The yield of the e,e,e-hexaacid of FIG. 4 was 13.29 mg (0.0129 mmol), 74.0% (isolated yield).

What is claimed is:

1. A method for synthesizing compounds of the formula

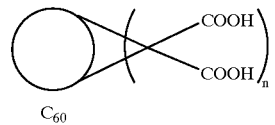

where $C_{60}$ is a $C_{60}$ fullerene, comprising the steps of:
(a) forming a macrocyclic malonate compound of the formula

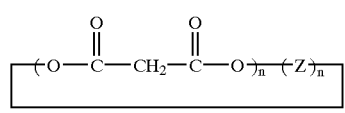

where each Z is the same or different and is a straight-chain or branched-chain aliphatic radical having from 1–30 carbon atoms which may be unsubstituted or monosubstituted or polysubstituted by identical or different substitutents, in which radicals up to every third $CH_2$ unit can be replaced by O or NR where R is alkyl having 1–20 carbon atoms or a chain containing unsubstituted or substituted aryl or other cyclic groups and n is an integer from 2 to 10;

(b) reacting said macrocyclic malonate compound with $C_{60}$ to form a macrocycle adduct of the formula

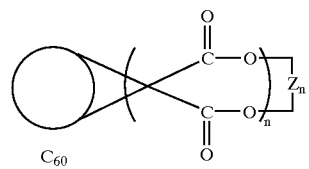

where the Z radicals are linked together to form said macrocycle adduct; and (c) hydrolyzing said macrocycle adduct to form a compound of the formula

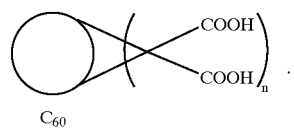

2. A method as recited in claim 1 wherein n is 2.

3. A method as recited in claim 1 wherein n is 3.

4. A method as recited in claim 1 wherein Z is a diol.

5. A method as recited in claim 1 wherein each Z is an alkanediol containing 8–10 carbon atoms.

6. A method as recited in claim 1 wherein Z is octanediol.

7. A method for synthesizing compounds of the formula

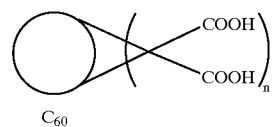

where $C_{60}$ is a $C_{60}$ fullerene, comprising the steps of:

(a) reacting a macrocyclic malonate compound of the formula

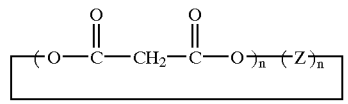

where each Z is the same or different and is a straight-chain or branched-chain, aliphatic radical having from 1–30 carbon atoms which may be unsubstituted or monosubstituted or polysubstituted by identical or different substitutents, in which radicals up to every third $CH_2$ unit can be replaced by O or NR where R is alkyl having 1–20 carbon atoms or a chain containing unsubstituted or substituted aryl or other cyclic groups and n is an integer from 2 to 10 with $C_{60}$ to form a macrocycle adduct of the formula

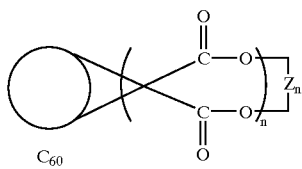

where the Z radicals are linked together to form said macrocycle adduct; and (b) hydrolyzing said macrocycle adduct to form a compound of the formula

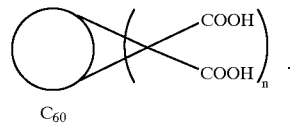

8. A method as recited in claim 7 wherein n is 2.
9. A method as recited in claim 7 wherein n is 3.
10. A method as recited in claim 7 wherein Z is a diol.
11. A method as recited in claim 7 wherein each Z is an alkanediol containing 8–10 carbon a toms.
12. A method as recited in claim 7 wherein Z is octanediol.
13. A method for synthesizing compounds of the formula

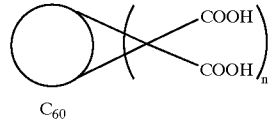

where $C_{60}$ is a $C_{60}$ fullerene, comprising the step of hydrolyzing a macrocycle adduct of the formula

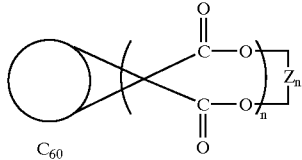

where the Z radicals are linked together to form said macrocycle adduct to form a compound of the formula

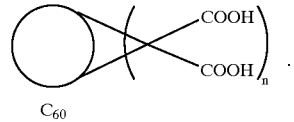

14. A method as recited in claim 13 wherein n is 2.
15. A method as recited in claim 13 wherein n is 3.
16. A method as recited in claim 13 wherein Z is a diol.
17. A method as recited in claim 13 wherein each Z is an alkanediol containing 8–10 carbon atoms.
18. A method as recited in claim 13 wherein Z is octanediol.

* * * * *

UNITED STATES PATENT AND TRADEMARK OFFICE
CERTIFICATE OF CORRECTION

PATENT NO. : 6,538,153 B1
DATED : March 25, 2003
INVENTOR(S) : Andreas Hirsch and Uwe Reuther It is certified that error appears in the above-identified patent and that said Letters Patent is hereby corrected as shown below:

<u>Column 14,</u>
Line 24, delete "a toms" and insert -- atoms --.

Signed and Sealed this

Twenty-third Day of December, 2003

JAMES E. ROGAN
*Director of the United States Patent and Trademark Office*